United States Patent [19]

Koerwer

[11] Patent Number: 4,498,920

[45] Date of Patent: Feb. 12, 1985

[54] TETRAHYDROTRIAZINES FOR AQUATIC HERBICIDAL USE

[75] Inventor: John F. Koerwer, Perkasie, Pa.

[73] Assignee: Union Carbide Corporation, Danbury, Conn.

[21] Appl. No.: 108,280

[22] Filed: Dec. 28, 1979

[51] Int. Cl.³ .............................................. A01N 43/64
[52] U.S. Cl. .......................................... 71/66; 71/67; 71/93
[58] Field of Search ................................. 71/93, 67, 66

[56] References Cited

PUBLICATIONS

Martin et al., J. Prakt. Chem., vol. 321 (2), 4-25-79, 315-319.

Primary Examiner—Catherine L. Mills
Attorney, Agent, or Firm—Clement J. Vicari

[57] ABSTRACT

Aquatic herbicidal compositions including tetrahydrotriazine compounds as the active toxicant. The invention also covers a method for the control of aquatic plant life which method utilizes as the active ingredient a tetrahydrotriazine compound.

20 Claims, No Drawings

TETRAHYDROTRIAZINES FOR AQUATIC HERBICIDAL USE

This invention relates to aquatic herbicides and more particularly to herbicides employed for the control of aquatic weeds.

Aquatic plants cause a variety of problems in lakes, pools, streams, irrigation systems, drainage canals, and in the cultivation of certain field crops. Thus in the recreational uses of water, aquatic plants interfere with swimming and fishing, foul outboard motors and often impart undesirable flavors and odors to the water. In streams, irrigation systems, and drainage canals, aquatic plants interfere with the flow of water, effect increased evaporation and seepage, and cause clogging of structures; while in the cultivation of such field crops as rice, aquatic plants compete for soil nutrients and sunlight resulting in considerable reductions of yields. While many mechanical methods for the control of undesirable aquatic plant life have been proposed and used in the past, such as dredging, underwater mowing, hand cleaning and chaining, only partial success has been obtained. In recent years there has been an increased interest in the chemical control of aquatic plants and as a result a few chemical compounds which are effective in controlling some of the undesirable aquatic plants have been discovered.

It is surprising, however, in view of the vast number of herbicidally active compounds which are known, only a limited number of chemical compounds exhibiting activity towards aquatic plant life have been found. In a study by Frank et al. 1963 Weeds 11:124–228, wherein ninety-one herbicides were tested for aquatic activity, it was found that little or no correlation between herbicidal activity toward terrestrial vegetation and activity for the control of aquatic plant life exists.

In addition, the use of herbicides for the control of aquatic weeds poses some unique problems due in part to differences in plant morphology and in part to the differences in the plant environment. When trees, brush and other terrestrial weeds are sprayed with herbicide, relatively large quantities of the herbicide-spray actually contact the foliage, stem and in some cases the roots (i.e., following precipitation). A similar direct application of herbicide spray to the exposed portion of aquatic vegetation is possible and for some weeds this is enough since the translocation process carries the herbicide throughout the plant. On the other hand for the submersed weeds and for the parts of the other weeds under the surface of the water the physical problem of carrying the herbicide directly to the plant without great dilution in a large mass of water is much greater than for the land weeds. Another problem is caused by differences in the plants themselves; a number of aquatic weeds such as the water hyacinth, pond lily, etc., are covered with a waxy coat which is only slightly permeable to aqueous solutions. Some of the other weeds such as elodea are highly permeable and nearly anything soluble in water can get into the plant. In selecting a herbicide, a formulation and an application method, one should consider all these factors in order to optimize the opportunity for the herbicide to be absorbed the the plant.

In view of the aquatic weed problem and the limited development of chemical compounds which can be used to control such weeds it is readily apparent that additional compounds and compositions useful for this purpose are urgently required.

In accordance with the present invention there is provided an aquatic herbicidal composition comprising an acceptable carrier and as an active toxicant a herbically effective amount of a compound selected from the group consisting of compounds having the general formula:

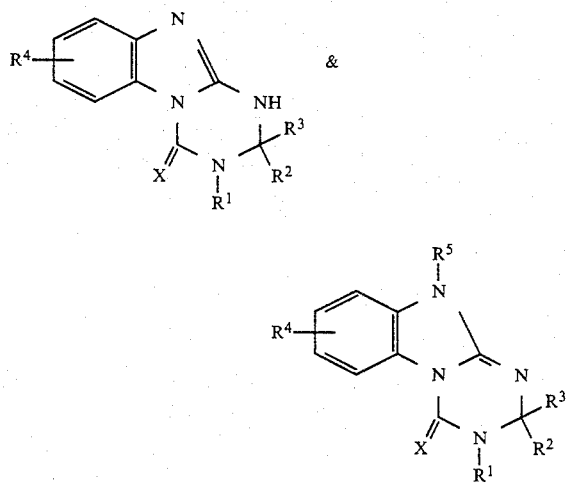

wherein $R^1$ is hydrogen, lower alkyl ($C_1$–$C_6$), cycloalkyl ($C_3$–$C_7$), lower alkenyl ($C_2$–$C_6$), lower alkynyl ($C_3$–$C_6$), haloalkyl ($C_1$–$C_6$) and alkoxyalkyl ($C_2$–$C_6$);

$R^2$ and $R^3$ individually are hydrogen, ketoalkyl ($C_3$–$C_5$), lower alkyl ($C_1$–$C_6$), cycloalkyl ($C_3$–$C_6$), alkoxyalkyl ($C_2$–$C_4$), alkenyl ($C_2$–$C_6$), haloalkyl ($C_1$–$C_6$), and acyl ($C_2$–$C_4$); $R^2$ and $R^3$ taken together can also form a spirocyclic ring of $C_3$–$C_5$ carbon atoms;

$R^4$ individually can be hydrogen, alkyl ($C_1$–$C_6$), a maximum of two halogens selected from the group consisting of Cl, F, and Br, alkoxyl ($C_1$–$C_4$), nitro, alkylthio ($C_1$–$C_4$) and alkylsulfonyl ($C_1$–$C_4$);

$R^5$ may be hydrogen, carbamoyl, N-alkylcarbamoyl ($C_2$–$C_{14}$), N-arylcarbamoyl, N-(substituted aryl)carbamoyl, N-haloalkylcarbamoyl ($C_2$–$C_{12}$), N-carboalkoxyalkylcarbamoyl, N-carboxyalkylcarbamoyl ($C_3$–$C_{14}$), N-alkoxyalkylcarbamoyl ($C_3$–$C_{14}$), N-arylsulfonylcarbamoyl, acyl($C_1$–$C_{14}$), aroyl, substituted aroyl, alkoxycarbonyl ($C_2$–$C_{14}$), aryloxycarbonyl, hydroxyacyl ($C_2$–$C_8$), alkoxyacyl ($C_3$–$C_9$), alkylthioacyl ($C_3$–$C_9$), alkylsulfonylacyl ($C_3$–$C_7$), N,N-dialkylaminoacyl ($C_4$–$C_{10}$), alkylsulfonyl ($C_1$–$C_{14}$), haloalkylsulfonyl ($C_1$–$C_{14}$), arylsulfonyl, substituted arylsulfonyl, alkyl ($C_1$–$C_{14}$), hydroxyalkyl ($C_1$–$C_8$), alkoxyalkyl ($C_2$–$C_9$), haloalkyl ($C_1$–$C_8$), cycloalkyl ($C_3$–$C_7$), alkenyl ($C_2$–$C_{14}$), cycloalkenyl ($C_5$–$C_7$), alkynyl ($C_2$–$C_{14}$), aryl and substituted aryl.

X is oxygen or sulfur.

Compositions falling within the above generic formula exhibit biological activity as aquatic herbicides to a greater or lesser extent. Some exhibit very powerful herbicidal activity against aquatic plants in extremely small dosages while others require larger dosages to be effective.

In general, the compounds which are preferred for aquatic herbicidal activity are those of the above structural formula wherein $R^1$ is alkyl ($C_1$–$C_4$);

$R^2$ and $R^3$ individually are alkyl ($C_1$-$C_3$) and cycloalkyl ($C_3$-$C_5$);

$R^4$ is hydrogen and alkyl ($C_1$-$C_4$);

$R^5$ is hydrogen, N-alkylcarbamoyl ($C_2$-$C_{14}$), N-arylcarbamoyl, N-(substituted aryl)carbamoyl, acyl ($C_1$-$C_{14}$), alkoxycarbonyl ($C_2$-$C_{14}$), alkylsulfonyl ($C_1$-$C_{14}$), arylsulfonyl and substituted arylsulfonyl.

X is 0.

Compounds which are most preferred are represented by structure and nomenclature as indicated below:

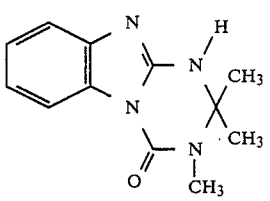

1,2-Dihydro-2,2,3-trimethyl-1,3,5-triazino[1,2-a]-benzimidazol-4(3H)-one (Compound 1)

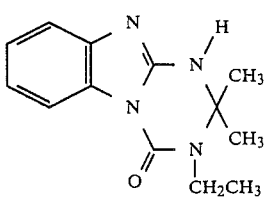

1,2-Dihydro-2,2-dimethyl-3-ethyl-1,3,5-triazino[1,2-a]-benzimidazol-4(3H)-one (Compound 2)

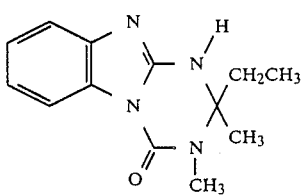

1,2-Dihydro-2,3-dimethyl-2-ethyl-1,3,5-triazino[1,2-a]-benzimidazol-4(3H)-one (Compound 3)

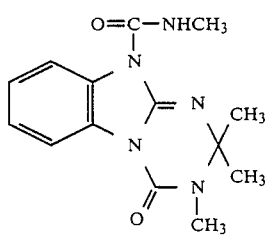

4-Oxo-2,3,4,10-tetrahydro-N,2,2,3-tetramethyl-1,3,5-triazino[1,2-a]benzimidazole-10-carboxamide (Compound 4)

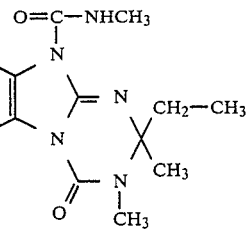

2-Ethyl-4-oxo-2,3,4,10-tetrahydro-N,2,3-trimethyl-1,3,5-triazine[1,2-a]benzimidazole-10-carboxamide (Compound 5)

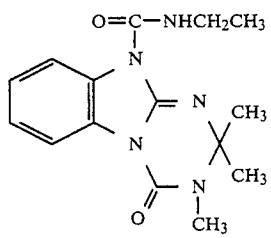

N-Ethyl-4-oxo-2,3,4,10-tetrahydro-2,2,3-trimethyl-1,3,5-triazino[1,2-a]benzimidazole-10-carboxamide (Compound 6)

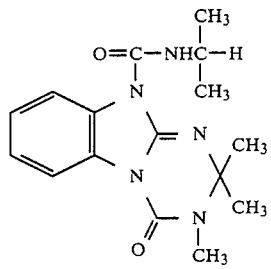

N-Isopropyl-4-oxo-2,3,4,10-tetrahydro-2,2,3-trimethyl-1,3,5-triazino[1,2a]benzimidazole-10-carboxamide (Compound 7)

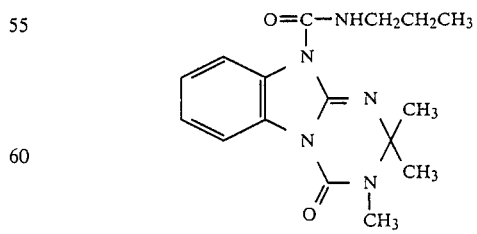

N-Propyl-4-oxo-2,3,4,10-tetrahydro-2,2,3-trimethyl-1,3,5-triazino[1,2-a]benzimidazole-10-carboxamide (Compound 8)

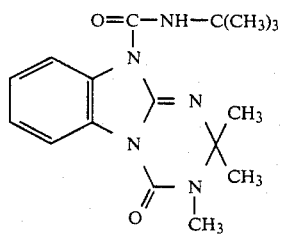

N-tert-Butyl-4-oxo-2,3,4,10-tetrahydro-2,2,3-trimethyl-1,3,5-triazino[1,2-a]benzimidazole-10-carboxamide (Compound 9)

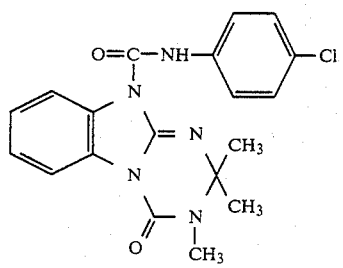

N-(4-Chlorophenyl)-4-oxo-2,3,4,10-tetrahydro-2,2,3-trimethyl-1,3,5-triazino[1,2-a]benzimidazole-10-carboxamide (Compound 10)

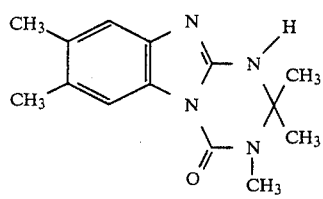

1,2-Dihydro-2,2,3,7,8-pentamethyl-1,3,5-triazino-[1,2-a]benzimidazol-4(3H)-one (Compound 11)

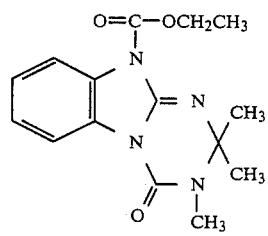

2,10-Dihydro-10-(ethoxycarbonyl)-2,2,3-trimethyl-1,3,5-triazino[1,2-a]benzimidazol-4(3H)-one (Compound 12)

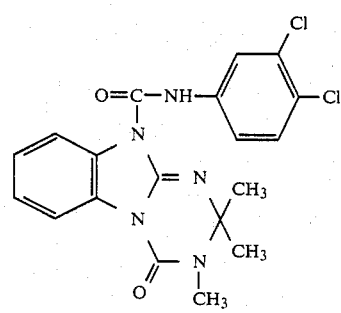

N-(3,4-Dichlorophenyl)-4-oxo-2,3,4,10-tetrahydro-2,2,3-trimethyl-1,3,5-triazino[1,2-a]benzimidazole-10-carboxamide (Compound 13)

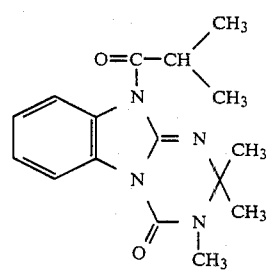

2,10-Dihydro-10-[(2-methyl)propanoyl]-2,2,3-trimethyl-1,3,5-triazino[1,2-a]benzimidazol-4(3H)-one (Compound 14)

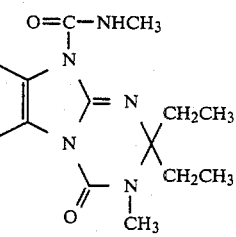

2,2-Diethyl-N,3-dimethyl-4-oxo-2,3,4,10-tetrahydro-1,3,5-triazino[1,2-a]benzimidazole-10-carboxamide (Compound 15)

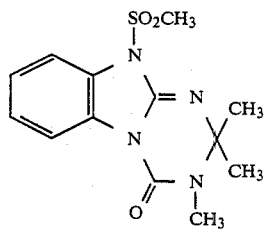

2,10-Dihydro-10-(methylsulfonyl)-2,2,3-trimethyl-1,3,5-triazino[1,2-a]benzimidazol-4(3H)-one (Compound 16)

1,2-Dihydro-2,2-dimethyl-1,3,5-triazino[1,2-a]-benzimidazol-4(3H)-one (Compound 17)

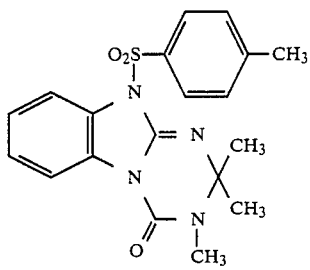

2,10-Dihydro-10-[(4-tolyl)sulfonyl]-2,2,3-trimethyl-1,3,5-triazino[1,2-a]benzimidazol- B 4(3H)-one (Compound 18)

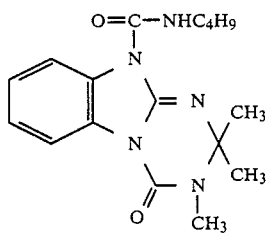

N-Butyl-4-oxo-2,3,4,10-tetrahydro-2,2,3-trimethyl-1,3,5-triazino[1,2-a]benzimidazole-10-carboxamide (Compound 19)

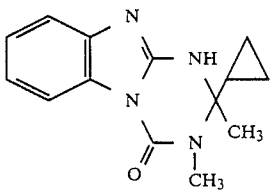

2-Cyclopropyl-1,2-dihydro-2,3-dimethyl-1,3,5-triazino[1,2-a]benzimidazol-4(3H)-one (Compound 20)

For convenience the $R^1$–$R^5$ substituents of the preferred compounds within the generic formula are as indicated in the following Table I.

TABLE I

| Compound | $R^1$ | $R^2$ | $R^3$ | $R^4$ | $R^5$ |
|---|---|---|---|---|---|
| 1 | CH₃ | CH₃ | CH₃ | —* | — |
| 2 | C₂H₅ | CH₃ | CH₃ | — | — |
| 3 | CH₃ | CH₃ | C₂H₅ | — | — |
| 4 | CH₃ | CH₃ | CH₃ | — | CH₃NHCO— |
| 5 | CH₃ | CH₃ | C₂H₅ | — | CH₃NHCO— |
| 6 | CH₃ | CH₃ | CH₃ | — | C₂H₅NHCO— |
| 7 | CH₃ | CH₃ | CH₃ | — | (CH₃)₂CHNHCO— |
| 8 | CH₃ | CH₃ | CH₃ | — | n-C₃H₇NHCO— |
| 9 | CH₃ | CH₃ | CH₃ | — | (CH₃)₃CNHCO— |
| 10 | CH₃ | CH₃ | CH₃ | — | Cl—⟨⟩—NHCO— |
| 11 | CH₃ | CH₃ | CH₃ | 7,8-(CH₃)₂ | — |
| 12 | CH₃ | CH₃ | CH₃ | — | C₂H₅OCO— |
| 13 | CH₃ | CH₃ | CH₃ | — | Cl,Cl—⟨⟩—NHCO— |
| 14 | CH₃ | CH₃ | CH₃ | — | (CH₃)₂CHCO— |
| 15 | CH₃ | C₂H₅ | C₂H₅ | — | CH₃NHCO— |
| 16 | CH₃ | CH₃ | CH₃ | — | CH₃SO₂— |
| 17 | H | CH₃ | CH₃ | — | — |
| 18 | CH₃ | CH₃ | CH₃ | — | CH₃—⟨⟩—SO₂— |
| 19 | CH₃ | CH₃ | CH₃ | — | n-C₄H₉NHCO— |
| 20 | CH₃ | ▷ | CH₃ | — | — |

*—designates hydrogen

In general, the novel tetrahydrotriazines of this invention can be prepared according to several methods illustrated by the following reaction schemes:

Method I

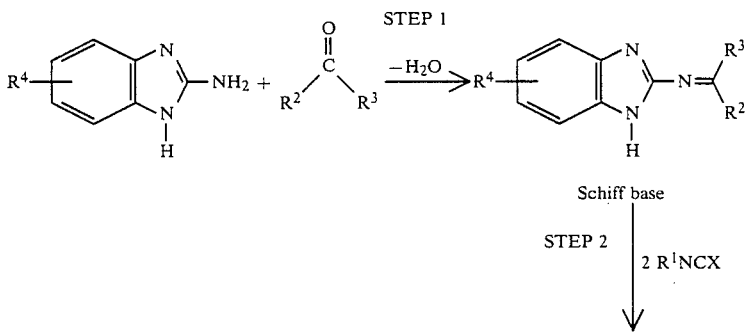

Schiff base

STEP 2 ↓ 2 R¹NCX

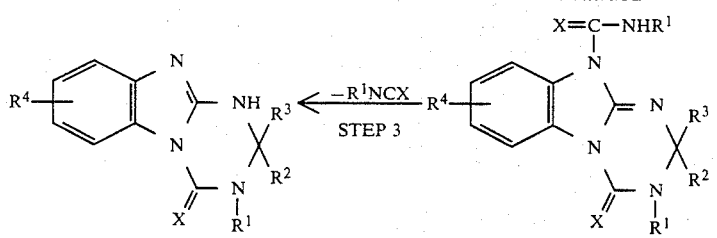

where X, and $R^1$-$R^4$ are as described previously.

A special case of Method I is that in which $R^1$=hydrogen and X=oxygen. In this case the isocyanic acid (HNCO) required for the second step is generated in situ by addition to the reaction mixture of N-chloroformamide, as shown below:

wherein Z may be halogen, perhalate (e.g. perchlorate, perbromate); X and $R^1$-$R^4$ are as described previously; R may be lower alkyl ($C_1$-$C_3$), aryl (e.g. phenyl or substituted phenyl), cycloalkyl ($C_3$-$C_7$), or the two R groups taken together may be cyclic in nature.

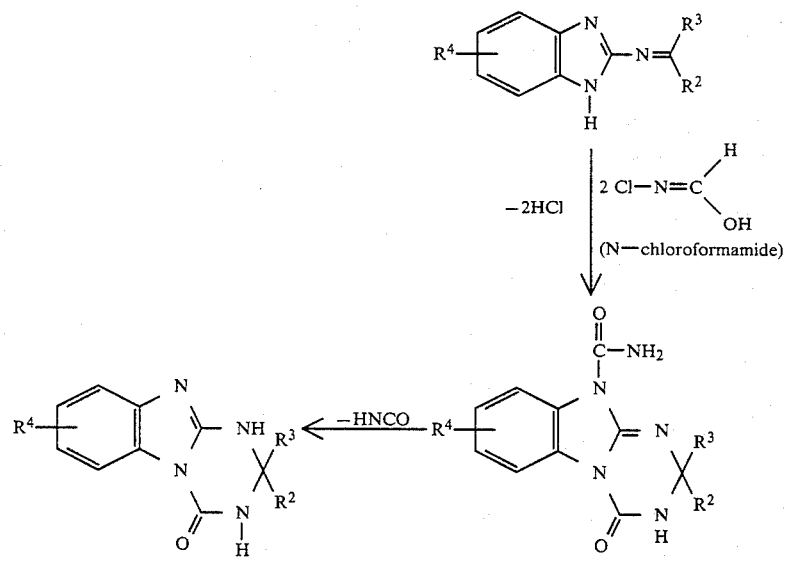

Method II

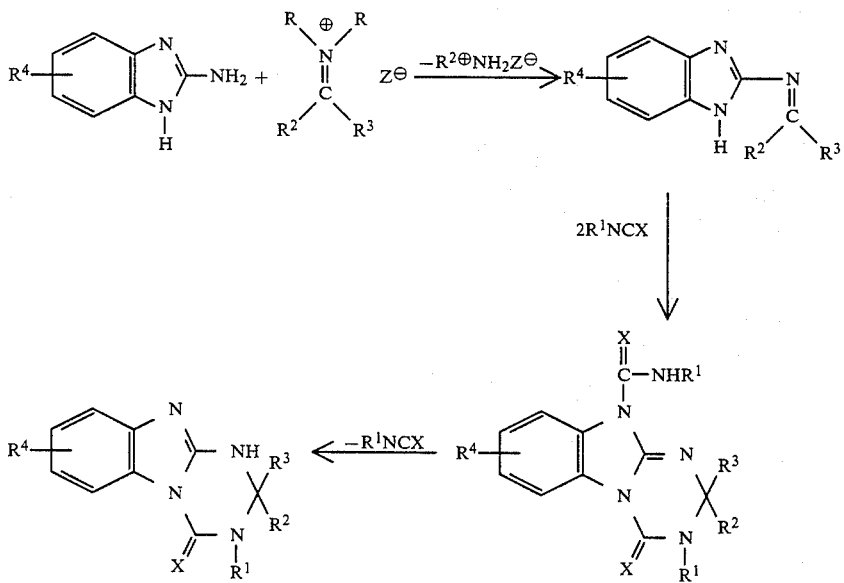

Method III

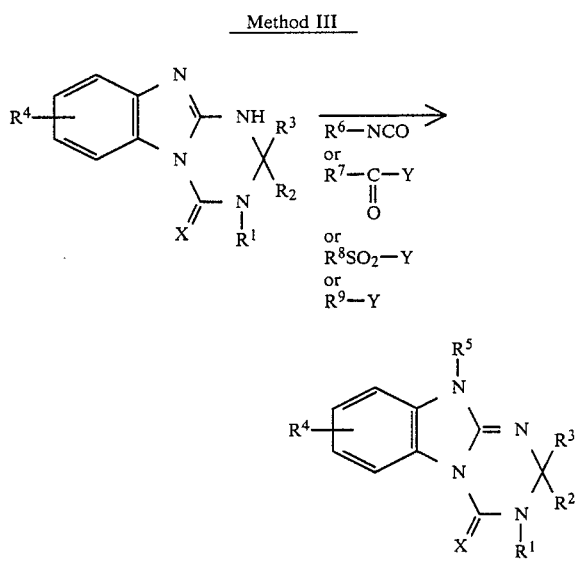

wherein X and $R^1$-$R^5$ are as defined previously; $R^6$ may be alkyl ($C_1$-$C_{14}$), aryl, substituted aryl, carboalkoxyalkyl, alkoxyalkyl, or hydrogen; $R^7$ may be alkyl ($C_1$-$C_{14}$), alkoxyalkyl, alkylthioalkyl, alkylsulfonylalkyl, dialkylaminoalkyl, aryl, cycloalkyl, substituted aryl, alkoxy ($C_1$-$C_{14}$), aryloxy, substituted aryloxy; $R^8$ may be alkyl ($C_1$-$C_{14}$), aryl, substituted aryl; $R^9$ may be alkyl ($C_1$-$C_{14}$), alkoxyalkyl, alkylthioalkyl, alkylsulfonylalkyl, dialkylaminoalkyl, aryl, cycloalkyl ($C_3$-$C_7$), alkenyl ($C_2$-$C_{14}$), cycloalkenyl ($C_5$-$C_7$), alkynyl ($C_2$-$C_{14}$); Y may be halogen (e.g. chlorine, bromine, iodine), arylsulfonate, alkylsulfonate.

In general, Method I involves three steps in the procedure for obtaining the final product, i.e. step 1, which is a Schiff base-forming reaction; step 2 which is a ring forming reaction involving the Schiff base formed in step 1; and step 3 which is a thermal or hydrolytic cleavage step to form the tetrahydrotriazine.

The step 1 Schiff base-forming reaction illustrated in Method I utilizes an appropriate substituted amine which is admixed with an appropriate ketone as indicated. The reaction is conducted in the presence of a solvent which advantageously can be the ketone reactant itself or alternatively the ketone can be employed with a cosolvent. Illustrative of solvents that can be utilized in the conduct of the Schiff base-forming reaction are tetrahydrofuran, dioxane and dimethoxyethane. The Schiff base-forming reaction step of Method I can be conducted in the temperature range of about 20°–200° C., preferably about 35° C. to 120° C. and in the pressure range of one atmosphere up to that required to contain the reaction at about 200° C. The concentration of the amine starting material in the mixture before reaction begins can be from 0.01 to 1.0 molar, preferably about 0.1 to 0.7 molar. In addition, the Schiff base-forming reaction step can, if desired, be conducted in the presence of an acid catalyst. Suitable acid catalysts include p-toluenesulfonic acid, trifluoroacetic acid, or zinc chloride.

As will be observed from the reaction scheme illustrated in Method I, it is necessary to remove the water formed as a by-product in the reaction. Water can be removed from the reaction by adding a drying agent or water scavenger to the reaction mixture. Illustrative of drying agents which can be used include molecular sieves (3A, 4A and 5A), calcium sulfate, calcium chloride and magnesium sulfate. Water may also be removed from the reaction by azeotropic distillation using a suitable cosolvent, examples of which include benzene, toluene and xylene. The Schiff base formed in Method I can be isolated or alternatively it can be subjected to the ring-forming reaction (step 2) in situ. If the Schiff base is isolated, it is thereafter subsequently dissolved in a suitable solvent and is then subjected to the illustrated ring-forming reaction. Examples of suitable solvents for this purpose include tetrahydrofuran, acetone, dioxane, dimethoxyethane, chloroform and methylene chloride. The ring-forming step of Method I can be conducted using from two to ten molar equivalents of a suitable isocyanate or isothiocyanate based on the number of moles of starting amine employed. In general, the ring-forming reaction step is conducted at a temperature range of about 0°–200° C., preferably about 25° to 80° C., and in a pressure range of about one atmosphere up to that required to contain the reaction at 200° C. The cleavage step 3 illustrated in Method I can be accomplished either hydrolytically or thermolytically. When the thermolytic method is used, the cyclized material from step 2 is placed in a suitable solvent; the resulting mixture is thereafter heated and the cleaved isocyanate is distilled from the mixture. Illustrative of the solvents utilized for the thermal cleavage step include petroleum hydrocarbons, xylene, diglyme and dimethylsulfoxide. The thermolytic cleavage of $R^1NCX$ may also occur during recovery of product from the ring-forming reaction (step 2) when, as may be practiced, the crude product is continually extracted with a hot inert solvent (such as hexane) as in a Soxhlet extraction system. Such a spontaneous thermolytic cleavage of $R^1NCX$ during workup frequently results in isolation of the final cleavage product alone, or of mixtures of the final product with the 10-N-carbamoylated precursor. The thermolytic reaction step 3 can be conducted at a temperature range of about 80°–250° C., preferably about 100° to 180° C., and in a pressure range of about 0.2–2.0, preferably 0.5 to 1.0 atmosphere. When the hydrolytic method is utilized, the cyclized material from step 2 is dissolved in a suitable solvent and the resulting solution is treated with water and an acid or base catalyst. Suitable solvents for the hydrolytic method include tetrahydrofuran, dioxane, acetone, dimethoxyethane and ethanol. Suitable acid catalysts include hydrochloric acid, sulfuric acid, trifluoroacetic acid and p-toluenesulfonic acid. Suitable base catalysts include sodium hydroxide, sodium carbonate, potassium hydroxide, potassium carbonate or triethylamine. The hydrolytic method can be conducted in a temperature range of about 0°–100° C., preferably about 25° to 60° C., and in the pressure range of one atmosphere up to that required to contain the reaction at 100° C.

The Schiff base-forming reaction illustrated in Method II can be conducted using a stoichiometric amount (i.e. one equivalent) of the iminium salt in a suitable solvent. Suitable solvents include tetrahydrofuran, dioxane, and dimethoxyethane. Alternatively, the Schiff base-forming reaction of Method II can be conducted using a catalytic amount of the iminium salt in an appropriate solvent. The appropriate solvent is the ketone $R^2COR^3$ or a mixture of this ketone and a suitable cosolvent. Suitable cosolvents include tetrahydrofuran, dioxane or dimethoxyethane. The Schiff base-forming reaction of Method II can be conducted in a temperature range of about 20°–200° C., preferably 35°–100° C., and in a pressure range of about 0.2 atmosphere up to that required to contain the reaction at about 200° C. The concentration of the starting material (amine) in the mixture before reaction begins may be from 0.01 to 1.0, preferably 0.1 to 0.7 molar. The Schiff base formed in Method II can be isolated or alternatively subjected to the ring-forming step in situ. Conditions for reaction in the ring-forming step and the subsequent cleavage step are as discussed for Method I.

The reaction illustrated by Method III represents the introduction of the substituent $R^5$ (when $R^5$ is other than hydrogen). This step can be conducted by combining the appropriate tricyclic material, obtained by Methods I and II, with the appropriate organic isocyanate, acyl halide, aroyl halide, sulfonyl halide or halide as defined previously in a suitable organic solvent in the presence of a suitable base catalyst or acid acceptor. Suitable organic solvents include acetone, tetrahydrofuran, dioxane, dimethoxyethane, methylene chloride and chloroform. Suitable catalysts or acid acceptors include triethylamine, pyridine, sodium carbonate, and potassium carbonate. The reaction may be conducted in the temperature range of 0°–100° C., preferably 25 to 50, and in the pressure range of 0.5–10.0, preferably 1 to 2 atmospheres. The concentration of the tricyclic material before reacton may be from 0.01–1.0, preferably 0.05 to 0.5 molar.

In general (for Methods I and II) the starting amines and their coreactants are known compounds or may be prepared through well-established chemical transformations. For example the 2-aminobenzimidazole reactant can be prepared by reaction of ortho-phenylenediamines with cyanamide according to the procedure of S. Weiss et al, Angewandte Chemie International Edition, Volume 12, page 841 (1973).

The ketones can be prepared by oxidation of the corresponding secondary alcohols as described by Arnold P. Lurie in Kirk-Othmer Encyclopedia of Chemical Technology, Second Edition, Volume 12, page 125, John Wiley and Sons, New York.

The following aquatic herbicidally active compounds are further illustrative of compounds within the purview of the above generic formula and which can be conveniently prepared by the methods of the invention simply by selecting appropriate reactants for use in the procedures described previously:

7,8-Dichloro-4-oxo-2,3,4,10-tetrahydro-N,2,2,3-tetramethyl-1,3,5-triazino[1,2-a]benzimidazole-10-carboxamide
1,2-Dihydro-8-nitro-2,2,3-trimethyl-1,3,5-triazino[1,2-a]benzimidazol-4(3H)-one
4-Oxo-N,2,2,3,8-pentamethyl-2,3,4,10-tetrahydro-1,3,5-triazino[1,2-a]benzimidazole-10-carboxamide
1,2-Dihydro-2,2,3,9-tetramethyl-1,3,5-triazino[1,2-a]benzimidazol-4(3H)-one
1,2-Dihydro-2,2,3,7-tetramethyl-1,3,5-triazino[1,2-a]benzimidazol-4(3H)-one
7,8-Dichloro-1,2-dihydro-1,3,5-triazino[1,2-a]benzimidazol-4(3H)-one
1,2-Dihydro-3-isopropyl-1,3,5-triazino[1,2-a]benzimidazol-4(3H)-one
2,2p-Diethyl-1,2-dihydro-1,3,5-triazino[1,2-a]benzimidazol-4(3H)-one
1,2-Dihydro-2,3,7,8-tetramethyl-2-trifluoromethyl-1,3,5-triazino[1,2-a]benzimidazol-4(3H)-one
1,2-Dihydro-7-ethoxy-2,2,3-trimethyl-1,3,5-triazino[1,2-a]benzimidazol-4(3H)-one
1,2p-Dihydro-2,2,3,8-tetramethyl-1,3,5-triazino[1,2-a]benzimidazol-4(3H)-one
2,2-Bis(trifluoromethyl)-1,2-dihydro-3-methyl-1,3,5-triazino[1,2-a]benzimidazol-4(3H)-one
1,2-Dihydro-2,3-dimethyl-2-trifluoromethyl-1,3,5-triazino[1,2-a]benzimidazol-4(3H)-one
1,2-Dihydro-2,2-dimethyl-3-trifluoromethyl-1,3,5-triazino[1,2-a]benzimidazol-4(3H)-one
1,2-Dihydro-2,3-dimethyl-1,3,5-triazino[1,2-a]benzimidazol-4(3H)-one
2,10-Dihydro-10-[(trifluoromethyl)sulfonyl]-2,2,3-trimethyl-1,3,5-triazino[1,2-a]benzimidazol-4(3H)-one
1,2-Dihydro-2-ethyl-2-methyl-1,3,5-triazino[1,2-a]benzimidazol-4(3H)-one
4-Oxo-2,3,4,10-tetrahydro-N,2,3-trimethyl-1,3,5-triazino[1,2-a]benzimidazole-10-carboxamide
1,2-Dihydro-2-propyl-1,3,5-triazino[1,2-a]benzimidazol-4(3H)-one
1,2-Dihydro-2-isopropyl-1,3,5-triazino[1,2-a]benzimidazol-4(3H)-one
1,2-Dihydro-3-propyl-1,3,5-triazino[1,2-a]benzimidazol-4(3H)-one
N,3-Dipropyl-4-oxo-2,3,4,10-tetrahydro-1,3,5-triazino[1,2-a]benzimidazole-10-carboxamide
1,2-Dihydro-2,7-dimethyl-1,3,5-triazino[1,2-a]benzimidazol-4(3H)-one
1,2-Dihydro-2,2,8-trimethyl-1,3,5-triazino[1,2-a]benzimidazol-4(3H)-one
1,2-Dihydro-2,2,7,8-tetramethyl-1,3,5-triazino[1,2-a]benzimidazol-4(3H)-one
1,2-Dihydro-3-ethyl-2-methyl-1,3,5-triazino[1,2-a]benzimidazol-4(3H)-one
3-Cyclopropyl-1,2-dihydro-2-methyl-1,3,5-triazino[1,2-a]benzimidazol-4(3H)-one
1,2-Dihydro-2-methyl-2-vinyl-1,3,5-triazino[1,2-a]benzimidazol-4(3H)-one
1,2-Dihydro-2-(2-propenyl)-1,3,5-triazino[1,2-a]benzimidazol-4(3H)-one
2-Acetyl-1,2-dihydro-2,3-dimethyl-1,3,5-triazino[1,2-a]benzimidazol-4(3H)-one
1,2-Dihydro-2,3-dimethyl-2-(2-oxopropyl)-1,3,5-triazino[1,2-a]benzimidazol-4(3H)-one
1,2-Dihydro-2-methoxymethyl-2-methyl-1,3,5-triazino[1,2-a]benzimidazol-4(3H)-one Examples illustrating the preparation of the compounds of the instant invention are contained in the copending application of C. E. Ward and R. E. Berthold, Ser. No. 108,284, filed concurrently herewith, assigned to a common assignee, and are repeated herein for purpose of convenience.

In Example 1, the procedures described are representative of those used to prepare benzimidazotetrahydros-triazines and their 10-N substituted derivatives. At the end of the Examples is Table II which indicates the $R^1$–$R^5$ and X values of each Example.

EXAMPLE 1

4-Oxo-2,3,4,10-tetrahydro-N,2,2,3-tetramethyl-1,3,5-triazino[1,2-a]benzimidazole-10-carboxamide (1A) and 1,2-Dihydro-2,2,3-trimethyl-1,3,5-triazino[1,2-a]benzimidazol-4(3H)-one(1B)

A 1-liter, round bottomed flask containing a magnetic stirrer bar was charged with 16 g (0.12 mole) of 2-aminobenzimidazole, 500 ml of acetone and 16 g of 3 A molecular sieves. The flask was fitted with a reflux condenser bearing a CaSO$_4$-drying tube after which the reaction mixture was stirred and heated at reflux. An additional 8 g of sieves were added on the second and fifth days of heating. Aliquots of the reaction mixture were withdrawn at 24 hour intervals, filtered, concentrated in vacuo and examined by NMR spectroscopy. After seven days the reaction was 58% complete. The reaction mixture was cooled to room temperature and methyl isocyanate (13.7 g, 0.24 mole) was added rapidly via syringe. The resulting mixture was stirred overnight at room temperature after which time it was concentrated under reduced pressure to afford a brittle solid. The solid was broken up, slurried in hexane and transferred into a Soxhlet extraction thimble. The thimble was placed in an extractor fitted to a 500-ml, round-bottomed flask containing a magnetic stirring bar and 400 ml of hexane. The material in the thimble was extracted until TLC (silica, 80:2:1, CHCl$_3$:MeOH:NH$_4$OH) showed none of the desired products remained (from 2-6 da.). The solids which had precipitated in the extraction pot were collected with suction and the resulting filtrate was concentrated to provide an additional small amount of material. The combined solids consisted of 14.9 g of a mixture of 1,2-dihydro-2,2,3-trimethyl-1,3,5-triazino[1,2-a]benzimidazol-4(3H)-one and its 10-N-methylcarbamoyl precursor 4-oxo-2,3,4,10-tetrahydro-N,2,2,3-tetramethyl-1,3,5-triazino[1,2-a]benzimidazole-10-carboxamide ($\geq 0.052$ mole of tricyclic products; $\geq 43\%$ yield).

The mixture was charged to a 500 ml, round-bottom flask containing a magnetic stirring bar. THF (300 ml) was added followed by 30 ml of 10% aqueous sodium hydroxide. The resulting heterogeneous mixture was stirred at room temperature for 6.5 hr. after which time TLC showed that only a trace of the 10-N-methylcarbamoyl material remained. The reaction mixture was transferred to a separatory funnel and washed with brine (3×). The organic phase was dried over potassium carbonate and concentrated under reduced pressure to afford 11.6 g of crude product 1B as a brown solid (42% yield based on 2-aminobenzimidazole). This material was recrystallized from acetone to yield 6.9 g of pure material (1B). An analytical sample prepared as described above sintered at 206° and had mp 209° C. (dec).

Anal. Calcd. for C$_{12}$H$_{14}$N$_4$O: C, 62.59; H, 6.13; N, 24.33. Found: C, 62,47; H, 6.16; N, 24.24.

Spectral data: nmr ($\delta$, CDCl$_3$) 1.73 (S, 6H, gem. methyls), 3.12 (S, 3H, N—CH$_3$), 6.96-7.40 (m, 3H, aromatic H), 7.83-8.16 (m, 1H, C-6 aromatic H); ir ($\nu_{max}^{CHCl_3}$) 31-3200 (broad, NH str.), 1710 (C=O str.), 1660 (C=N str.), 1620, 1600, 1500, 1460, 1420, 1380, 1310, 1290, 1230, 1170, 1140, 1100, 1050, 890 cm$^{-1}$; uv ($\lambda_{max}^{EtOH}$) 282 nm ($\epsilon$ 7600), 287 nm ($\epsilon$ 7830).

EXAMPLE 2

1,2-Dihydro-2,2-dimethyl-3-ethyl-1,3,5-triazino[1,2-a]benzimidazol-4(3H)-one

The title compound was prepared from 2-aminobenzimidazole, acetone and ethyl isocyanate by the procedure described in the first paragraph of Example 1. In this preparation, a 10-N-methylcarbamoyl derivative was not isolated and the subject compound was recovered from the Soxhlet extraction and recrystallized from acetone to give a solid, mp above 300° C. (dec).

The confirmatory elemental analysis is shown in Table III.

EXAMPLE 3

2,2-Dimethyl-N,3-dipropyl-4-oxo-2,3,4,10-tetrahydro-1,3,5-triazino[1,2-a]benzimidazole-10-carboxamide The subject compound was prepared by reaction of 2-aminobenzimidazole, acetone and propyl isocyanate with workup all essentially as described in the first paragraph of Example 1. The product was purified by column chromatography on silica, eluting with chloroform, giving, on evaporation, white crystals, mp 72°-74° C. The confirmatory elemental analysis is shown in Table III.

EXAMPLE 4

1,2-Dihydro-2,2-dimethyl-3-propyl-1,3,5-triazino[1,2-a]benzimidazol-4(3H)-one

The title compound was prepared by hydrolysis of the precursor compound of Example 3 in the presence of 10% aqueous sodium hydroxide and THF employing the method of paragraph 2, Example 1. The product was crystallized from acetone to give colorless prisms, mp 170° C. (dec). The confirmatory elemental analysis is shown in Table III.

EXAMPLE 5

3-Butyl-1,2-dihydro-2,2-dimethyl-1,3,5-triazino[1,2-a]benzimidazol-4(3H)-one

The title compound was prepared from 2-aminobenzimidazole, acetone, and n-butyl isocyanate, conducting the initial condensation and subsequent base hydrolysis of the intermediate 10-N-butylcarbamoyl precursor as described in Example 1. The solid product had mp 142°-149° C. (dec.). The confirmatory elemental analysis is shown in Table III.

EXAMPLE 6

1,2-Dihydro-2,2-dimethyl-1,3,5-triazino[1,2-a]benzimidazol-4(3H)-one

A mixture of 16 g (0.12 mole) of 2-aminobenzimidazole, 100 ml of acetone and 16 g of 3 A molecular sieves was stirred and heated under reflux, adding 8 g of additional sieves after 24 hours. Refluxing was continued for a total period of 3 days, after which the mixture was allowed to cool and a solution of 4.77 g (0.06 mole) of N-chloroformamide (1) in ~25 ml. of acetone added dropwise with stirring. The mixture was warmed to the reflux point several times and the rate of N-chloroformamide addition adjusted to keep the temperature just below the reflux point. An additional 50 ml of acetone were added to facilitate stirring of the thickening reaction mixture. Upon completion of the feed, the reaction flask was fitted with a drying tube and the mixture stirred for 3 days at room temperature. The reaction mixture was then evaporated under reduced pressure to give 9.3 g of a tan solid. The latter was extracted with boiling acetone to separate an insoluble fraction and the acetone solution evaporated to give the crude solid product. The latter material was chromatographed on silica, eluting with CHCl$_3$/CH$_3$OH (80:5). Fractions 3 through 8 were combined and evaporated to give 3.9 g of product, mp 178°-180° C. (dec). elemental analysis is shown in Table III.

EXAMPLE 6

1,2-Dihydro-2,2-dimethyl-1,3,5-triazino[1,2-a]-benzimidazol-4(3H)-one

A mixture of 16 g (0.12 mole) of 2-aminobenzimidazole, 100 ml of acetone and 16 g of 3 A molecular sieves was stirred and heated under reflux, adding 8 g of additional sieves after 24 hours. Refluxing was continued for a total period of 3 days, after which the mixture was allowed to cool and a solution of 4.77 g (0.06 mole) of N-chloroformamide (1) in ~25 ml. of acetone added dropwise with stirring. The mixture was warmed to the reflux point several times and the rate of N-chloroformamide addition adjusted to keep the temperature just below the reflux point. An additional 50 ml of acetone were added to facilitate stirring of the thickening reaction mixture. Upon completion of the feed, the reaction flask was fitted with a drying tube and the mixture stirred for 3 days at room temperature. The reaction mixture was then evaporated under reduced pressure to give 9.3 g of a tan solid. The latter was extracted with boiling acetone to separate an insoluble fraction and the acetone solution evaporated to give the crude solid product. The latter material was chromatographed on silica, eluting with $CHCl_3/CH_3OH$ (80:5). Fractions 3 through 8 were combined and evaporated to give 3.9 g of product, mp 178°–180° C. (dec). mp 113°–119° C. (dec.). The confirmatory elemental analysis is shown in Table III.

EXAMPLE 9

1,2-Dihydro-2,3-dimethyl-2-ethyl-1,3,5-triazino[1,2-a]-benzimidazol-4(3H)-one

The 10-N-methylcarbamoyl precursor prepared in Example 8 was hydrolyzed in the presence of 10% aqueous sodium hydroxide and THF according to the procedure of paragraph 2, Example 1. The product was obtained as crystals from acetone, mp 202° C. (dec). The confirmatory elemental analysis is shown in Table III.

EXAMPLE 10

3-Butyl-4-oxo-2,3,4,10-tetrahydro-N,2,2-trimethyl-1,3,5-triazino[1,2-a]benzimidazole-10-carboxamide by carbamoylation of the parent heterocycle 3-Butyl-1,2-dihydro-2,2-dimethyl-1,3,5-triazino[1,2-a]benzimidazol-4(3H)-one (2.5 g, 0.0092 mole) from Example 5 was suspended in a solution of triethylamine (0.5 ml) in 50 ml of acetone. The resulting mixture was stirred with a magnetic stirring bar, and 0.54 ml (0.0092 mole) of methyl isocyanate added, in one portion, by a syringe. The resulting mixture was stirred at room temperature, becoming a yellow solution after about 10 minutes, and stirring was continued overnight. Solvent was removed from the mixture under reduced pressure and the resulting solid chromatographed on a silica column giving 1.8 g of title compound, mp 124°–129° C.

Anal. Calcd. for $C_{17}H_{23}N_5O_2$: C, 61.99; H, 7.04; N, 21.26. Found: C, 62.11; H, 7.04; N, 21.16.

Spectral data: nmr ($\delta$, $CDCl_3$) 0.70–1.13 (m, 3H, butyl $CH_3$), 1.13–1.83 (m, 10H, $CH_3$—C—$CH_3$ and C—$CH_2CH_2$—C), 2.98 (d, 3H, J=4Hz, N—$CH_3$), 3.13–3.67 (m, 2H, N—$CH_2$—), 6.97–7.33 (m, 2H, aromatic H), 7.77–8.10 (m, 1H, aromatic H), 8.10–8.43 (m, 1H, aromatic), 9.03–9.55 (broad, 1H, NH); ir ($\nu_{max}^{CHCl_3}$) 3225, 2960, 2875, 1710, 1660, 1470, 1390, 1370, 1310, 1290, 1190, 1160, 1040, 1020, 970, 930 $cm^{-1}$.

EXAMPLE 11

N-Ethyl-4-oxo-2,3,4,10-tetrahydro-2,2,3-trimethyl-1,3,5-triazino[1,2-a]benzimidazole-10-carboxamide The title compound was prepared by reaction of 1,2-dihydro-2,2,3-trimethyl-1,3,5-triazino[1,2-a]benzimidazol-4(3H)-one (see Example 1 (B)) with ethyl isocyanate according to the general procedure of Example 10. The product, mp 127°–131° C., was obtained as a white solid in 96% yield. The confirmatory elemental analysis is shown in Table III.

EXAMPLE 12

N-Propyl-4-oxo-2,3,4,10-tetrahydro-2,2,3-trimethyl-1,3,5-triazino[1,2-a]benzimidazole-10-carboxamide The title compound was prepared from 1,2-dihydro-2,2,3-trimethyl-1,3,5-triazino[1,2-a]benzimidazol-4(3H)-one (Example 1 (B)) and n-propyl isocyanate according to the procedure of Example 10. The confirmatory elemental analysis for the product, mp 85°–87° C., is shown in Table III.

EXAMPLE 13

N-Isopropyl-4-oxo-2,3,4,10-tetrahydro-2,2,3-trimethyl-1,3,5-triazino[1,2-a]benzimidazole-10-carboxamide The procedure of Example 10 was used to prepare the title compound from 1,2-dihydro-2,2,3-trimethyl-1,3,5-triazino[1,2-a]benzimidazol-4(3H)-one and isopropyl isocyanate. The product crystallized as a white solid, mp 93°–96° C. The confirmatory elemental analysis is shown in Table III.

EXAMPLE 14

N-Butyl-4-oxo-2,3,4,10-tetrahydro-2,2,3-trimethyl-1,3,5-triazino[1,2-a]benzimidazole-10-carboxamide The procedure of Example 10 was used to prepare the title compound from 1,2-dihydro-2,2,3-trimethyl-1,3,5-triazino[1,2-a]benzimidazol-4(3H)-one and n-butyl isocyanate. The confirmatory elemental analysis for the product, mp 95°–97° C., is shown in Table III.

EXAMPLE 15

N-(4-Chlorophenyl)-4-oxo-2,3,4,10-tetrahydro-2,2,3-trimethyl-1,3,5-triazino[1,2-a]benzimidazole-10-carboxamide The procedure of Example 10 was used to prepare the title compound from 1,2-dihydro-2,2,3-trimethyl-1,3,5-triazino[1,2-a]benzimidazol-4(3H)-one and 4-chlorophenyl isocyanate. The confirmatory elemental analysis for the product, mp 206°–211° C., is shown in Table III.

EXAMPLE 16

N-tert-Butyl-4-oxo-2,3,4,10-tetrahydro-2,2,3-trimethyl-1,3,5-triazino[1,2-a]benzimidazole-10-carboxamide The procedure of Example 10 was used to prepare the title compound from 1,2-dihydro-2,2,3-trimethyl-1,3,5-triazino[1,2-a]benzimidazol-4(3H)-one and tert-butyl isocyanate. The white solid product melted at 209° C. with decomposition. The confirmatory elemental analysis is shown in Table III.

EXAMPLE 17

10-Acetyl-2,10-dihydro-2,2,3-trimethyl-1,3,5-triazino-[1,2-a]benzimidazol-4(3H)-one A 250-ml, round-bottomed flask containing a magnetic stirring bar was charged with 2.45 g (0.0106 mole) of 1,2-dihydro-2,2,3-trimethyl-1,3,5-triazino[1,2-a]benzimidazol-4-(3H)-one, 150 ml of acetone and 1.53 ml of triethylamine. Acetyl chloride (0.86 g, 0.0110 mole) was added rapidly via syringe to the resulting solution. The mixture was stirred for two hours at room temperature after which time a white precipitate of triethylammonium hydrochloride was visible. Examination of the reaction mixture by TLC (silica, 80:2:1, $CHCl_3:CH_3OH:NH_4OH$) showed that only a trace of starting material remained. The mixture was concentrated in vacuo and the resulting solid was taken up in methylene chloride. The resulting solution was washed with water (3 times) brine, dried ($MgSO_4$) and concentrated under reduced pressure to afford 1.5 g (52% yield) of a white solid which was analytically pure, mp 159°–62° C.

Anal. Calcd. for $C_{14}H_{16}N_4O_2$: C, 61.75; H, 5.92; N, 20.58. Found: C, 61.70; H, 5.71; N, 20.55.

Spectral data: nmr ($\delta$, $CDCl_3$) 1.57 (S, 6H, gem. methyls), 2.70 (S, 3H, $COCH_3$), 3.03 (S, 3H, $N-CH_3$), 6.93–7.37 (m, 2H, aromatic H), 7.77–8.07 (m, 1H, C-6 aromatic H), 8.07–8.40 (m, 1H, C-9 aromatic H); ir ($\nu_{max}^{CHCl_3}$) 3000, 1720 (C=O str.), 1600, 1480, 1380, 1350, 1290, 1190, 1150 cm$^{-1}$.

EXAMPLE 18

N-Cyclohexyl-4-oxo-2,3,4,10-tetrahydro-2,2,3-trimethyl-1,3,5-triazino[1,2-a]benzimidazole-10-carboxamide The subject compound was prepared from 1,2-dihydro-2,2,3-trimethyl-1,3,5-triazino[1,2-a]benzimidazol-4(3H)-one and cyclohexyl isocyanate according to the method of Example 10. The confirmatory elemental analysis for the product, mp 114°–116° C., is shown in Table III.

EXAMPLE 19

2,10-Dihydro-2,2,3,10-tetramethyl-1,3,5-triazino[1,2-a]-benzimidazol-4(3H)-one A mixture of 2.0 g (0.0087 mole) 1,2-dihydro-2,2,3-trimethyl-1,3,5-triazino[1,2-a]benzimidazol-4(3H)-one, 1.1 ml (0.0174 mole) methyl iodide, anhydrous potassium carbonate (1 gram) and acetone (100 ml) was heated under reflux, with stirring, overnight. After refluxing had continued 21 hours an additional 1 ml of methyl iodide was added and solids removed from the mixture by suction filtration. The filtrate was evaporated under reduced pressure and the resulting residue dissolved in ethyl acetate, washed with water, then with brine and dried over $MgSO_4$, filtered and solvent stripped off to give B 1.8 g of crude product. Purification by high pressure liquid chromatography gave a solid, mp 79°–82° C.

Anal. Calcd. for $C_{13}H_{16}N_4O$: C, 63.91; H, 6.60; N, 22.94. Found: C, 63.79; H, 6.55; N, 22.71.

Spectral data: nmr ($\delta$, DMSO-$d_6$)1.5(S, 6H, gem. methyls), 3.0 (S, 3H, $N-CH_3$), 3.25 (S, 3H, $N-CH_3$), 6.8–7.2 (m, 3H, aromatic H), 7.55–7.84 (m, 1H, aromatic H); ir ($\nu_{max}^{CHCl_3}$) 2955, 1680 (strong, C=N), 1615, 1485, 1478, 1421, 1380, 1200 cm$^{-1}$.

EXAMPLE 20

2,10-Dihydro-10-(ethoxycarbonyl)-2,2,3-trimethyl-1,3,5-triazino[1,2-a]benzimidazol-4(3H)-one The title compound was prepared from 1,2-dihydro-2,2,3-trimethyl-1,3,5-triazino[1,2-a]benzimidazol-4(3H)-one (2.35 g, 0.0102 mole), ethyl chloroformate (1.1 ml, 0.0102 mole) and triethylamine (1 ml, 0.0102 mole) by reaction in 150 ml of acetone solvent according to the general method of Example 17. The yellowish, crude product was chromatographed on a Waters LC 500 instrument to give 1.62 g of a clear oil which crystallized to a solid, mp 84°–86° C. The confirmatory elemental analysis for the product is shown in Table III.

EXAMPLE 21

N-(3,4-Dichlorophenyl)-4-oxo-2,3,4,10-tetrahydro-2,2,3-trimethyl-1,3,5-triazino[1,2-a]benzimidazole-10-carboxamide The procedure of Example 10 was employed to prepare the title compound from 1,2-dihydro-2,2,3-trimethyl-1,3,5-triazino[1,2-a]benzimidazol-4(3H)-one and 3,4-dichlorophenyl isocyanate. The confirmatory elemental analysis for the product, mp 198°–200° C., is shown in Table III.

EXAMPLE 22

2,10-Dihydro-10-[(2-methyl)propanoyl]-2,2,3-trimethyl-1,3,5-triazino[1,2-a]benzimidazol-4(3H)-one The general procedure of Example 17 was used to prepare the title compound by reaction of 1,2-dihydro-2,2,3-trimethyl-1,3,5-triazino[1,2-a]benzimidazol-4(3H)-one, isobutyryl chloride and triethylamine in acetone solution. The product was isolated as a yellowish oil which crystallized to a solid, mp 99°–102° C. The confirmatory elemental analysis is shown in Table III.

EXAMPLE 23

2,2-Diethyl-N,3-dimethyl-4-oxo-2,3,4,10-tetrahydro-1,3,5-triazino[1,2-a]benzimidazole-10-carboxamide(23 A) and

2,2-Diethyl-1,2-dihydro-3-methyl-1,3,5-triazino-[1,2-a]benzimidazol-4(3H)-one(23B)

The title compounds were prepared by reaction of 2-aminobenzimidazole, diethyl ketone and methyl isocyanate, employing the procedure of the first paragraph of Example 1. Liquid chromatographic separation of the reaction products give both the 10-carboxamide (23A), mp 114°–125° C., and the decarbamoylated compound (23B), mp 215° C. (dec.). The confirmatory elemental analyses are shown in Table III.

EXAMPLE 24

2,10-Dihydro-10-[(4-tolyl)sulfonyl]-2,2,3-trimethyl-1,3,5-triazino[1,2-a]benzimidazol-4(3H)-one The general procedure of Example 17 was used to prepare the title compound by reaction of 1,2-dihydro-2,2,3-trimethyl-1,3,5-triazino[1,2-a]benzimidazol-4(3H)-one, para-toluenesulfonyl chloride and triethylamine in acetone solution. After recrystallization from ethyl acetate, the product formed colorless prisms, mp 147°–149° C. The confirmatory elemental analytical data are shown in Table III.

EXAMPLE 25

7,8-Dichloro-1,2-dihydro-2,2,3-trimethyl-1,3,5-triazino[1,2-a]benzimidazol-4(3H)-one Reaction of 2-amino-5,6-dichlorobenzimidazole with acetone and methyl isocyanate according to the procedure of Example 1, first paragraph, provided the title compound. In this case, a 10-N-methylcarbamoyl derivative was not isolated from the reaction mixture. The product was recrystallized from acetone to give a solid, mp 220° C. (dec.). The confirmatory elemental analysis is shown in Table III.

EXAMPLE 26

N,3-Dimethyl-4-oxo-2,3,4,10-tetrahydrospiro[1,3,5-triazino[1,2-a]benzimidazole-2,1'-cyclopentane]-10-carboxamide Employing the general procedure of Example 1, paragraph 1,2-aminobenzimidazole (16 g, 0.012 mole), methyl isocyanate (14 ml, 0.024 mole) and cyclopentanone (250 ml) were reacted using 250 ml of tetrahydrofuran as a cosolvent with the excess cyclopentanone. Workup of the reaction mixture by liquid chromatography using $CH_2Cl_2/CH_3OH$ (80/1: V/V) gave the product as a solid, mp 150° C. (dec). The confirmatory elemental analysis is shown in Table III.

EXAMPLE 27

3-Methyl-4-oxo-1,2,3,4-tetrahydrospiro[1,3,5-triazino-[1,2-a]benzimidazole-2,1'-cyclopentane]

The reaction product of Example 26 was hydrolyzed by 10% aqueous sodium hydroxide and THF to give the title compound, employing the procedure of Example 1, paragraph 2. The product was recrystallized from acetone to give a solid, mp 180°–182° C. The confirmatory elemental analysis is shown in Table III.

EXAMPLE 28

1,2-Dihydro-2,3-dimethyl-2-(2-methylpropyl)-1,3,5-triazino[1,2-a]benzimidazol-4(3H)-one 2-Aminobenzimidazole, methyl isobutyl ketone and ethyl isocyanate were reacted as in Example 26 using an equal volume of THF as cosolvent with the excess ketone. Working up the reaction mixture gave a crude fraction of the 10-N-methylcarbamoyl derivative of the title compound which was not purified but hydrolyzed by the 10% NaOH-THF procedure of Example 1, paragraph 2. The title compound was obtained as a solid, mp 150°–157° C. The confirmatory elemental analysis is shown in Table III.

EXAMPLE 29

1,2-Dihydro-2,2,3,7,8-pentamethyl-1,3,5-triazino-[1,2-a]benzimidazol-4(3H)-one 2-Amino-5,6-dimethylbenzimidazole monohydrate, acetone and methyl isocyanate were reacted, conducting the initial condensation and subsequent base hydrolysis of the intermediate 10-N-methylcarbamoyl precursor as described in Example 1. The title compound was recovered and purified by liquid chromatography to give a solid, mp 211° C. (dec.). The confirmatory elemental analysis is shown in Table III.

EXAMPLE 30

2,10-Dihydro-10-(methylsulfonyl)-2,2,3-trimethyl-1,3,5-triazino[1,2-a]benzimidazol-4(3H)-one The general procedure of Example 17 was employed to prepare the title compound by reaction of 1,2-dihydro-2,2,3-trimethyl-1,3,5-triazino[1,2-a]benzimidazol-4(3H)-one, methanesulfonyl chloride and triethylamine in acetone solution. The title compound was isolated and purified by liquid chromatography giving a solid, mp 147° C. (dec.). The confirmatory elemental analysis is shown in Table III.

EXAMPLE 31

1,2-Dihydro-2,2,3-trimethyl-1,3,5-triazino[1,2-a]-benzimidazol-4(3H)-thione

The subject compound was prepared by reacting 2-aminobenzimidazole, acetone and methyl isothiocyanate by the procedure described in the first paragraph of Example 1, above. In this case, a 10-N methylthiocarbamoyl derivative was not obtained and the subject compound was recovered directly from the Soxhlet extraction and recrystallized from acetone to give crystals, mp 186° C. (with decomposition).

Anal. Calcd. for $C_{12}H_{14}N_4S$: C, 58.51; H, 5.73; N, 22.75; Found: C, 58.65; H, 5.62; N, 22.98; Spectral data: nmr ($\delta$, $CDCl_3$) 1.75 (S, 6H, gem. methyls), 3.53 (S, 3H, N—$CH_3$), 6.90–7.37 (m, 3H, aromatic H), 8.60–9.00 (m, 1H, aromatic H); ir ($\nu_{max}^{CHCl_3}$) 2700–3300 (broad, NH), 1670 (C=N str), 1590, 1491, 1455, 1404, 1365, 1325, 1268, 1232, 1172, 1152, 1138, 1121, 1088, 1043, 1015, 972, 885, 752, 735 cm$^{-1}$; $^{13}$C nmr ($\delta$, $CDCl_3$), 27.0 (gem dimethyls), 34.0 (N—$CH_3$), 73.0

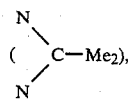

115.5, 117, 121, 124.9 (aromatic carbons bearing H), 132.5, 142.9, 149.5 (carbons without H), 174 (C=S).

EXAMPLE 32

2-Cyclopropyl-1,2-dihydro-2,3-dimethyl-1,3,5-triazino-[1,2-a]benzimidazol-4(3H)-one 2-Aminobenzimidazole, cyclopropyl methyl ketone and methyl isocyanate were reacted as in Example 26 using THF as a cosolvent with the excess ketone. Working up the reaction mixture gave none of the expected 10-N-methylcarbamoyl derivative of the title compound but, rather, the title compound itself, recrystallized from acetone to give a solid, mp 200° C. (dec.). The confirmatory elemental analysis is shown in Table III.

EXAMPLE 33

4-Oxo-2,3,4,10-tetrahydro-N,2,2,3-tetramethyl-1,3,5-triazino[1,2-a]benzimidazole-10-carboxamide: Preparation by iminium salt procedure (illustrating Method II, above)

To a stirred solution of 2 g. (0.015 mole) of 2-aminobenzimidazole in 50 ml of acetone was added a solution of 2.99 g (0.015 mole) of N-isopropylidenepyrrolidinium perchlorate[(2)] in acetone, in one portion, followed by an 8-g portion of 3A molecular sieves. The resulting mixture was heated under reflux with stirring for approximately 23 hours, allowed to cool, 1.71 g (0.03 mole) of methyl isocyanate added via syringe, and the mixture then stirred overnight at room temperature. The reaction mixture was filtered and the filtrate freed of solvent under reduced pressure. The resulting residue was taken up in chloroform, washed with water, dried (MgSO$_4$) and vacuum stripped to give 3.4 g of a dark oil, identified by its proton NMR spectrum as the desired product. The latter was purified on a high-pressure liquid chromatograph, eluting with CH$_2$Cl$_2$/CH$_3$OH (97.6%/2.4% by volume), giving 1.25 g (33% yield) of 4-oxo-2,3,4,10-tetrahydro-N,2,2,3-tetramethyl-1,3,5-triazino[1,2-a]benzimidazole-10-carboxamide.

(2) Prepared by the procedure of N. J. Leonard and J. V. Paukstelis as described in J. Org. Chem. 28, 3021 (1963).

The above compound may be used as a herbicide or, alternatively, may be converted to the herbicidal 1,2-dihydro-2,2,3-trimethyl-1,3,5-triazino[1,2-a]-benzimidazol-4(3H)-one as described in Example 1.

TABLE II

Structural Key

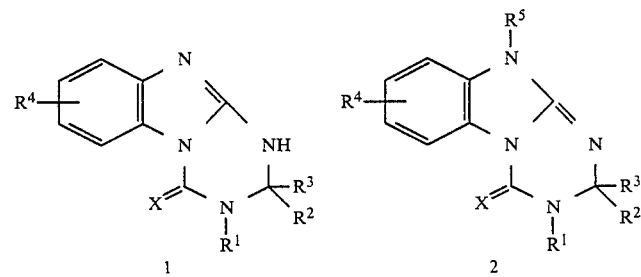

| Example | R$^1$ | R$^2$ | R$^3$ | R$^4$ | R$^5$ | X |
|---|---|---|---|---|---|---|
| 1(A) | CH$_3$ | CH$_3$ | CH$_3$ | H | CH$_3$NHCO— | O |
| 1(B) | CH$_3$ | CH$_3$ | CH$_3$ | H | —* | " |
| 2 | C$_2$H$_5$ | CH$_3$ | CH$_3$ | H | — | " |
| 3 | n-C$_3$H$_7$ | CH$_3$ | CH$_3$ | H | n-C$_3$H$_7$NHCO— | " |
| 4 | n-C$_3$H$_7$ | CH$_3$ | CH$_3$ | H | — | " |
| 5 | n-C$_4$H$_9$ | CH$_3$ | CH$_3$ | H | — | " |
| 6 | H | CH$_3$ | CH$_3$ | H | — | " |
| 7 | (CH$_3$)$_2$CH— | CH$_3$ | CH$_3$ | H | (CH$_3$)$_2$CHNHCO— | " |
| 8 | CH$_3$ | CH$_3$ | C$_2$H$_5$ | H | CH$_3$NHCO— | " |
| 9 | CH$_3$ | CH$_3$ | C$_2$H$_5$ | H | — | " |
| 10 | n-C$_4$H$_9$ | CH$_3$ | CH$_3$ | H | CH$_3$NHCO— | " |
| 11 | CH$_3$ | CH$_3$ | CH$_3$ | H | C$_2$H$_5$NHCO— | " |
| 12 | CH$_3$ | CH$_3$ | CH$_3$ | H | (CH$_3$)$_2$CHNHCO— | " |
| 13 | CH$_3$ | CH$_3$ | CH$_3$ | H | n-C$_3$H$_7$NHCO— | " |
| 14 | CH$_3$ | CH$_3$ | CH$_3$ | H | n-C$_4$H$_9$NHCO— | " |
| 15 | CH$_3$ | CH$_3$ | CH$_3$ | H | Cl—⟨C$_6$H$_4$⟩—NHCO— | " |
| 16 | CH$_3$ | CH$_3$ | CH$_3$ | H | (CH$_3$)$_3$CNHCO— | " |
| 17 | CH$_3$ | CH$_3$ | CH$_3$ | H | CH$_3$CO— | " |
| 18 | CH$_3$ | CH$_3$ | CH$_3$ | H | ⟨S-thienyl⟩—NHCO— | " |
| 19 | CH$_3$ | CH$_3$ | CH$_3$ | H | CH$_3$ | " |
| 20 | CH$_3$ | CH$_3$ | CH$_3$ | H | C$_2$H$_5$OCO— | " |
| 21 | CH$_3$ | CH$_3$ | CH$_3$ | H | Cl,Cl—⟨C$_6$H$_3$⟩—NHCO— | " |
| 22 | CH$_3$ | CH$_3$ | CH$_3$ | H | (CH$_3$)$_2$CHCO— | " |
| 23(A) | CH$_3$ | C$_2$H$_5$ | C$_2$H$_5$ | H | CH$_3$NHCO— | " |
| 23(B) | CH$_3$ | C$_2$H$_5$ | C$_2$H$_5$ | H | — | " |
| 24 | CH$_3$ | CH$_3$ | CH$_3$ | H | CH$_3$—⟨C$_6$H$_4$⟩—SO$_2$— | " |
| 25 | CH$_3$ | CH$_3$ | CH$_3$ | 7,8-Cl$_2$ | —* | " |
| 26 | CH$_3$ | —(CH$_2$)$_4$— | | H | CH$_3$NHCO— | " |

TABLE II-continued

Structural Key

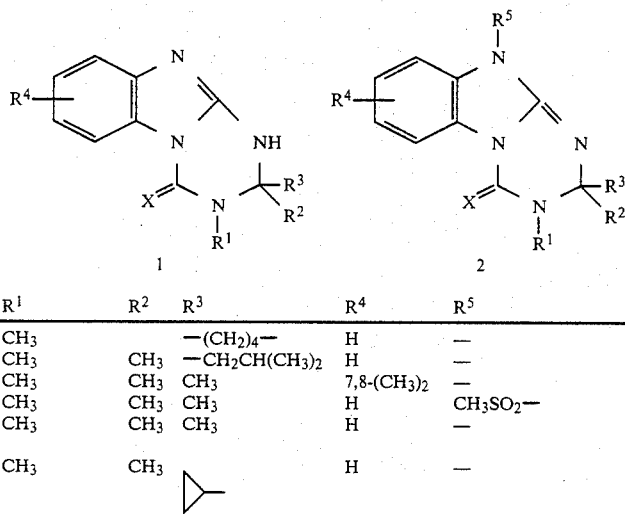

| Example | R¹ | R² | R³ | R⁴ | R⁵ | X |
|---|---|---|---|---|---|---|
| 27 | CH₃ | —(CH₂)₄— | | H | — | " |
| 28 | CH₃ | CH₃ | —CH₂CH(CH₃)₂ | H | — | " |
| 29 | CH₃ | CH₃ | CH₃ | 7,8-(CH₃)₂ | — | " |
| 30 | CH₃ | CH₃ | CH₃ | H | CH₃SO₂— | " |
| 31 | CH₃ | CH₃ | CH₃ | H | — | S |
| 32 | CH₃ | CH₃ | ▷— | | H | — | O |

*— designates hydrogen

TABLE III

Physical Properties and Elemental Analyses

| Compound Example No. | mp °C. | Molec. Form. | Calcd. C | Calcd. H | Calcd. N | Found C | Found H | Found N |
|---|---|---|---|---|---|---|---|---|
| 1B | 209 dec | C₁₂H₁₄N₄O | 62.59 | 6.13 | 24.33 | 62.47 | 6.16 | 24.24 |
| 2 | >300 dec | C₁₃H₁₆N₄O | 63.91 | 6.60 | 22.93 | 63.81 | 6.74 | 22.91 |
| 3 | 72–74 | C₁₈H₂₅N₅O₂ | 62.9 | 7.3 | 20.3 | 63.09 | 7.00 | 20.21 |
| 4 | 170 dec | C₁₄H₁₈N₄O | 65.1 | 7.0 | 21.7 | 65.04 | 6.94 | 21.72 |
| 5 | 142–49 dec | C₁₅H₂₀N₄O | 66.1 | 7.4 | 20.6 | 64.98 | 7.99 | 19.66 |
| 6 | 178–80 dec | C₁₁H₁₂N₄O | 61.09 | 5.60 | 25.91 | 61.00 | 5.49 | 25.38 |
| 7 | 80–89 | C₁₈H₂₅N₅O₂ | 62.9 | 7.3 | 20.4 | 63.19 | 7.41 | 19.67 |
| 8 | 113–19 dec | C₁₅H₁₉N₅O₂ | 59.78 | 6.35 | 23.24 | 59.38 | 6.16 | 23.41 |
| 9 | 202 dec | C₁₃H₁₆N₄O | 63.91 | 6.60 | 22.94 | 63.64 | 6.54 | 23.08 |
| 1A | 164 dec | C₁₄H₁₇N₅O₂ | 58.52 | 5.97 | 24.38 | 58.60 | 5.91 | 24.04 |
| 10 | 124–29 | C₁₇H₂₃N₅O₂ | 61.99 | 7.04 | 21.26 | 62.11 | 7.04 | 21.16 |
| 11 | 127–31 | C₁₅H₁₉N₅O₂ | 59.78 | 6.35 | 23.24 | 59.82 | 6.39 | 23.43 |
| 12 | 85–87 | C₁₆H₂₁N₅O₂ | 60.93 | 6.71 | 22.21 | 60.69 | 6.85 | 22.36 |
| 13 | 93–96 | C₁₆H₂₁N₅O₂ | 60.93 | 6.71 | 22.21 | 60.67 | 6.56 | 22.08 |
| 14 | 95–97 | C₁₇H₂₃N₅O₂ | 61.98 | 7.04 | 21.26 | 61.84 | 7.11 | 21.02 |
| 15 | 206–11 dec | C₁₉H₁₈ClN₅O₂ | 59.45 | 4.73 | 18.25 | 58.86 | 4.66 | 17.93 |
| 16 | 209 dec | C₁₇H₂₃N₅O₂ | 61.98 | 7.04 | 21.26 | 61.94 | 7.02 | 21.25 |
| 17 | 159–62 | C₁₄H₁₆N₄O₂ | 61.75 | 5.92 | 20.58 | 61.70 | 5.71 | 20.55 |
| 18 | 114–16 | C₁₉H₂₅N₅O₂ | 64.20 | 7.09 | 19.71 | 64.19 | 6.86 | 19.57 |
| 19 | 79–82 | C₁₃H₁₆N₄O | 63.91 | 6.60 | 22.94 | 63.79 | 6.55 | 22.71 |
| 29 | 211 dec | C₁₄H₁₈N₄O | 65.09 | 7.02 | 21.69 | 65.21 | 6.91 | 21.72 |
| 20 | 84–86 | C₁₅H₁₈N₄O₃ | 59.59 | 6.00 | 18.53 | 59.40 | 5.93 | 18.90 |
| 21 | 198–200 | C₁₉H₁₇Cl₂N₅O₂ | 54.55 | 4.10 | 16.74 | 54.37 | 4.02 | 16.74 |
| 22 | 99–102 | C₁₆H₂₀N₄O₂ | 63.98 | 6.71 | 18.65 | 63.79 | 6.67 | 18.66 |
| 23A | 114–25 | C₁₆H₂₁N₅O₂ | 60.93 | 6.71 | 22.21 | 60.81 | 6.62 | 21.84 |
| 23B | 215 dec | C₁₄H₁₈N₄O | 65.09 | 7.02 | 21.69 | 65.04 | 6.96 | 21.93 |
| 26 | 150 dec | C₁₆H₁₉N₅O₂ | 61.32 | 6.11 | 22.35 | 61.28 | 6.11 | 22.11 |
| 27 | 180–82 | C₁₄H₁₆N₄O | 65.60 | 6.29 | 21.86 | 65.67 | 6.25 | 21.89 |
| 28 | 150–57 | C₁₅H₂₀N₄O | 66.15 | 7.40 | 20.57 | 65.80 | 7.33 | 20.38 |
| 30 | 147 dec | C₁₃H₁₆N₄O₃S | 50.63 | 5.23 | 18.17 | 49.87 | 5.16 | 17.93 |
| 31 | 186 dec | C₁₂H₁₄N₄S | 58.51 | 5.73 | 22.75 | 58.65 | 5.64 | 22.98 |
| 32 | 200 dec | C₁₄H₁₆N₄O | 65.62 | 6.29 | 21.86 | 65.35 | 6.21 | 21.67 |
| 25 | 220 dec | C₁₂H₁₂Cl₂N₄O | 48.17 | 4.04 | 18.73 | 48.08 | 3.88 | 19.13 |
| 24 | 147–149 | C₁₉H₂₀N₄O₃S | 59.36 | 5.24 | 14.57 | 59.22 | 5.21 | 14.53 |

The compounds utilized in the compositions of the present invention are particularly effective in controlling the following weed species:

| | |
|---|---|
| Duckweed | (*Lemna minor*) |
| Salvinia | (*Salvinia rotundifolia*) |
| Cabomba | (*Cabomba caroliniana*) |
| Milfoil | (*Myriophyllum heterophyllum*) |
| Najas | (*Najas flexilis*) |
| Parrot Feather | (*Myriophyllum brasiliense*) |
| Sago Pondweed | (*Potamogeton pectinatus*) |
| Hydrilla | (*Hydrilla verticillata*) |
| Algae | |

For practical use in controlling aquatic plant life, the active compounds of this invention can be formulated into compositions which comprise an inert carrier or a diluent and a toxic amount of the compound. Such compositions, which can also be called formulations, enable the active compound to be applied conveniently to the site of the aquatic weed infestation in any desired quantity. These compositions can be liquids such as solutions or emulsifiable concentrates, or solids such as granules, wettable powders or pellets.

Solutions of the active compound of this invention can usually be prepared by dissolving the compound in a common organic solvent such as dimethylformamide, acetone and dimethylsulfoxide.

Emulsifiable concentrates comprise the active compound of this invention, a solvent and an emulsifier. The emulsifiers most commonly used are nonionic or mixtures of nonionic with anionic surface active agents.

Solid formulations such as granules can be prepared by impregnating the active compound, usually dissolved in a suitable solvent, onto and into granulated carriers such as the attapulgites or the vermiculites usually of a particle size range of from about 0.3 to about 5 mm. For example, a typical granular formulation can be prepared by charging absorbent granules into a tumbler mixer and then applying a solution of the active compound in the form of a fine spray until the desired concentration of active ingredient is obtained.

Wettable powders consist of admixtures of finely divided powders of an inert carrier, such as talc, clay, silica, pyrophyllite and the like and the active compound to which wetting agents have been added. Such formulations are usually prepared by grinding and blending the ingredients until a free flowing dust of the desired particle size is obtained.

Pelletized formulations consist of the active compound, a solid inert carrier and a binding agent. Suitable binding agents are hardenable materials, such as vinyl chloride-vinyl acetate copolymers, hydrocarbon resins, alkyd resins, drying oil, resin esters, varnishes, phenolic resins, and any of the film forming polymeric materials commonly used in the paint industry. Pellets are usually prepared by mixing the active compound, the inert carrier and the binding agent which can be in a solution form, until a paste results. This paste is then extruded into pellets of any desired size or shape and is then hardened by evaporating the solvent, heat curing the polymeric material or other methods as required. Such pelletized formulations often have the advantage of releasing the active ingredient at a controlled rate resulting in better and longer lasting control of aquatic plants.

The concentration of the active compound of this invention in the various formulations will vary greatly with the type of formulation and the purpose for which it is designed, but generally the formulations will contain from about 0.05 to about 95 percent by weight of the active compound of this invention.

The compositions of this invention can be applied to the site of the aquatic plant life infestation in a manner recognized by the art. One method for control of aquatic plant life comprises contacting said plant life with a toxic amount of the compound of this invention or a composition which comprises a carrier and the active compound of this invention. Another method for the control of aquatic plant life comprises contacting the water in which said plant life grows with a toxic amount of the compound or composition heretofore described. Yet another method comprises treating the soil in which aquatic weeds grow with a described composition.

The quantity of active compound required to control aquatic plant life is dependent on a variety of factors such as the hardiness of the particular plant species, method of application, depth and flow of water, density of phytoplankton, temperature, water hardness, pH and the like. Generally, a rate of from about 0.05 to about 50 lb. of active compound per acre or, a concentration of about 0.1 to about 100 ppm in the water in which the weeds are growing can be required for good control of aquatic weeds. For example, to control submerged plants in static water a concentration of only about 5 ppm or less can be sufficient, however, to control the same plants in rapidly moving water, a concentration of up to 100 ppm may be required.

The effectiveness of the compound of the present invention as aquatic herbicides was demonstrated by experiments wherein a wide variety of compounds of the invention were applied to aquatic weeds in an active state of growth according to the following procedure:

To each of several large glass jars are added 3 liters of water. A solution prepared by dissolving 15 mg. of each test compound in acetone is then added to each jar to provide a concentration of 5 parts per million. When various concentrations of the test compound are desired, 30 mg. of the test compound are dissolved in 10 milliliters of acetone. This stock solution of each chemical to be tested as an aquatic herbicide is prepared in such a manner that 1 (one) milliliter of stock solution, when added to three (3) liters of water, will give a concentration of 1 ppm (3 mg.) active ingredient. Similarly, a 2 ppm concentration would require 2 milliliters of stock solution, 4 ppm-4 milliliters, etc.

A sample of various aquatic weeds, as specified in the table are placed in each jar. The jars and their contents are maintained at about 74° F. Three weeks later the results are recorded in terms of a scale ranging from 0 to 10, 0 representing no injury and 10 representing complete kill.

The results are indicated in Table IV.

TABLE IV

| Compound/Example No. | Duckweed | Salvinia | Elodea | Potamogeton | Algae |
|---|---|---|---|---|---|
| 1A | 10 | 10 | 10 | 3 | 0 |
| 1B | 10 | 10 | 10 | 0 | 10 |
| 2 | 6 | 10 | 10 | 3 | 10 |
| 3 | 3 | 10 | 3 | 0 | 0 |
| 4 | 3 | 10 | 3 | 0 | 0 |
| 5 | 0 | 10 | 3 | 0 | 0 |
| 6 | 10 | 10 | 6 | 0 | 0 |
| 7 | 0 | 8 | 9 | 6 | 0 |
| 8 | 10 | 10 | 10 | 6 | 0 |
| 9 | 10 | 10 | 10 | 3 | 0 |
| 10 | 0 | 3 | 6 | 0 | 0 |
| 11 | 10 | 10 | 10 | 0 | 10 |
| 12 | 10 | 10 | 0 | 0 | 10 |
| 13 | 10 | 10 | 10 | 3 | 10 |
| 14 | 10 | 10 | 10 | 0 | 0 |
| 15 | 10 | 10 | 10 | 3 | 0 |
| 16 | 10 | 10 | 10 | 0 | 0 |
| 17 | 10 | 10 | 0 | 3 | 0 |
| 18 | 10 | 10 | 6 | 3 | 0 |
| 19 | 6 | 10 | 0 | 3 | 0 |
| 20 | 10 | 10 | 0 | 3 | 10 |
| 21 | 10 | 10 | 10 | 3 | 10 |
| 22 | 10 | 10 | 6 | 0 | 10 |
| 23A | 10 | 10 | 3 | 8 | 0 |
| 23B | 10 | 10 | 6 | 8 | 0 |

Relative Aquatic Activity at 5 ppm, where 0 = No Effect and 10 = Complete Kill Test Species TABLE IV-continued Relative Aquatic Activity at 5 ppm, where
0 = No Effect and 10 = Complete Kill

| Compound/<br>Example No. | Duck-<br>weed | Salvinia | Elodea | Potamogeton | Algae |
|---|---|---|---|---|---|
| 26 | 0 | 10 | 3 | 0 | 0 |
| 27 | 3 | 10 | 0 | 0 | 0 |
| 28 | 3 | 10 | 6 | 6 | 0 |
| 29 | 10 | 10 | 10 | 3 | 10 |
| 30 | 10 | 10 | 8 | 8 | 0 |
| 31 | 3 | 10 | 3 | 3 | 0 |
| 32 | 6 | 10 | 10 | 3 | 0 |

The above data clearly demonstrates the efficacy of the compounds of the invention as aquatic herbicides. Advantageously, aquatic life such as goldfish, minnows, turtles, snails and the like, are not appreciably affected by the compounds in customarily employed concentrations. As a matter of fact, goldfish toxicity tests conducted under conventional procedures indicated substantially no affect against goldfish at p.p.m. of 0.2 and 2.0 after a period of two days.

What is claimed is:

1. A method for the control of aquatic plant life which comprises applying to the aquatic plant life a composition comprising an inert carrier, and as an essential active ingredient, in a quantity toxic to aquatic plant life, a compound selected from the group consisting of compounds having the general formula:

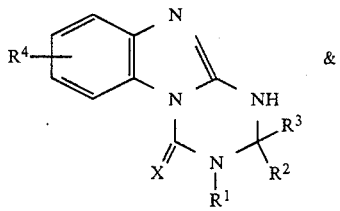 &

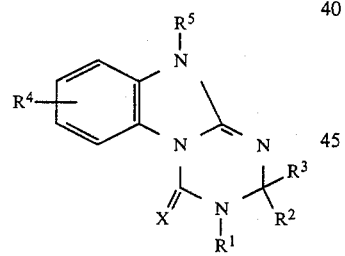

wherein
R$^1$ is hydrogen, lower alkyl (C$_1$-C$_6$), cycloalkyl (C$_3$-C$_7$) lower alkenyl (C$_2$-C$_6$), lower alkynyl (C$_3$-C$_6$), haloalkyl (C$_1$-C$_6$) and alkoxyalkyl (C$_2$-C$_6$);

R$^2$ and R$^3$ individually are hydrogen, ketoalkyl (C$_3$-C$_5$), lower alkyl (C$_1$-C$_6$), cycloalkyl (C$_3$-C$_6$), alkoxyalkyl (C$_2$-C$_4$), alkenyl (C$_2$-C$_6$), haloalkyl (C$_1$-C$_6$), and acyl (C$_2$-C$_4$); R$^2$ and R$^3$ taken together can also form a spirocyclic ring of C$_3$-C$_5$ carbon atoms;

R$^4$ individually can be H, alkyl (C$_1$-C$_6$), a maximum of two halogens selected from the group consisting of Cl, F, and Br, alkoxyl (C$_1$-C$_4$), nitro, alkylthio (C$_1$-C$_4$) and alkylsulfonyl (C$_1$-C$_4$);

R$^5$ may be hydrogen, carbamoyl, N-alkylcarbamoyl (C$_2$-C$_{14}$), N-arylcarbamoyl, N-(substituted aryl)carbamoyl, N-haloalkylcarbamoyl (C$_2$-C$_{12}$), N-carboalkoxyalkylcarbamoyl, N-carboxyalkylcarbamoyl (C$_3$-C$_{14}$), N-alkoxyalkylcarbamoyl (C$_3$-C$_{14}$), N-arylsulfonylcarbamoyl, acyl(C$_1$-C$_{14}$), aroyl, substituted aroyl, alkoxycarbonyl (C$_2$-C$_{14}$), aryloxycarbonyl, hydroxyacyl (C$_2$-C$_8$) alkoxyacyl (C$_3$-C$_9$), alkylthioacyl (C$_3$-C$_9$), alkylsulfonylacyl (C$_3$-C$_7$), N,N-dialkylaminoacyl (C$_4$-C$_{10}$), alkylsulfonyl (C$_1$-C$_{14}$), haloalkylsulfonyl (C$_1$-C$_{14}$), arylsulfonyl, substituted arylsulfonyl, alkyl (C$_1$-C$_{14}$), hydroxyalkyl (C$_1$-C$_8$), alkoxyalkyl (C$_2$-C$_9$), haloalkyl (C$_1$-C$_8$), cycloalkyl (C$_3$-C$_7$), alkenyl (C$_2$-C$_{14}$), cycloalkenyl (C$_5$-C$_7$), alkynyl (C$_2$-C$_{14}$), aryl and substituted aryl;

X is oxygen or sulfur.

2. A method according to claim 1 wherein R$^1$ is alkyl containing 1-4 carbon atoms.

3. A method according to claim 1 wherein R$^1$ is methyl.

4. A method according to claim 1 wherein R$^2$ and R$^3$ individually are alkyl containing 1-3 carbon atoms and cycloalkyl containing 3-5 carbon atoms.

5. A method according to claim 1 wherein R$^4$ is alkyl containing 1-4 carbon atoms.

6. A method according to claim 1 wherein R$^4$ is hydrogen.

7. A method according to claim 1 wherein R$^5$ is hydrogen, N-alkylcarbamoyl (C$_2$-C$_{14}$), N-arylcarbamoyl, N-(substituted aryl)carbamoyl, acyl(C$_1$-C$_{14}$), alkoxycarbonyl (C$_2$-C$_{14}$), alkylsulfonyl (C$_1$-C$_{14}$), arylsulfonyl and substituted arylsulfonyl.

8. A method for the control of aquatic plant life which comprises applying to the aquatic plant life a composition comprising an inert carrier, and as an essential active ingredient, in a quantity toxic to aquatic plant life, a compound selected from the group consisting of compounds having the general formula:

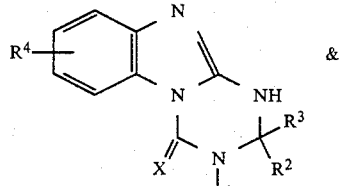 &

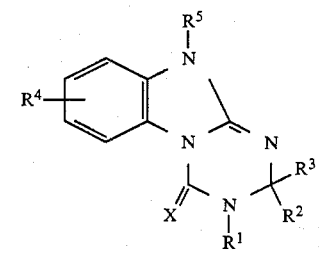

wherein X is oxygen or sulfur;
wherein
R$^1$ is hydrogen, lower alkyl (C$_1$-C$_6$), cycloalkyl (C$_3$-C$_7$) lower alkenyl (C$_2$-C$_6$), lower alkynyl (C$_3$-C$_6$), haloalkyl (C$_1$-C$_6$) and alkoxyalkyl (C$_2$-C$_6$);

R$^2$ and R$^3$ individually are alkyl containing 1-3 carbon atoms and cycloalkyl containing 3-5 carbon atoms, R$^4$ is H or alkyl containing 1-4 carbon atoms, and R$^5$ is hydrogen, carbamoyl, N-alkylcarbamoyl (C$_2$-C$_{14}$), N-arylcarbamoyl, N-(substituted aryl)carbamoyl, N-haloalkylcarbamoyl (C$_2$-C$_{12}$), N- carboalkoxyalkylcarbamoyl, N-carboxyalkylcarbamoyl (C$_3$–C$_{14}$), N-alkoxyalkylcarbamoyl (C$_3$–C$_{14}$), N-arylsulfonylcarbamoyl, acyl (C$_1$–C$_{14}$), aroyl, substituted aroyl, alkoxycarbonyl (C$_2$–C$_{14}$), aryloxycarbonyl, hydroxyacyl (C$_2$–C$_8$), alkoxyacyl (C$_3$–C$_9$), alkylthioacyl (C$_3$–C$_9$), alkylsulfonylacyl (C$_3$–C$_7$), N,N-dialkylaminoacyl (C$_4$–C$_{10}$), alkylsulfonyl (C$_1$–C$_{14}$), haloalkylsulfonyl (C$_1$–C$_{14}$), arylsulfonyl, substituted arylsulfonyl, alkyl (C$_1$–C$_{14}$), hydroxyalkyl (C$_1$–C$_8$), alkoxyalkyl (C$_2$–C$_9$), haloalkyl (C$_1$–C$_8$), cycloalkyl (C$_3$–C$_7$), alkenyl (C$_2$–C$_{14}$), cycloalkenyl (C$_5$–C$_7$), alkynyl (C$_2$–C$_{14}$), aryl and substituted aryl.

9. A method according to claim 8 wherein R$^1$ is alkyl containing 1–4 carbon atoms.

10. A method according to claim 8 wherein R$^1$ is methyl.

11. A method according to claim 8 wherein R$^5$ is hydrogen, N-alkylcarbamoyl (C$_2$–C$_{14}$), N-arylcarbamoyl, N-(substituted aryl)carbamoyl, acyl(C$_1$–C$_{14}$), alkoxycarbonyl (C$_2$–C$_{14}$), alkylsulfonyl (C$_1$–C$_{14}$), arylsulfonyl and substituted arylsulfonyl.

12. A method for the control of aquatic plant life which comprises applying to the aquatic plant life a composition comprising an inert carrier, and as an essential active ingredient, in a quantity toxic to aquatic plant life, a compound selected from the group consisting of compounds having the general formula:

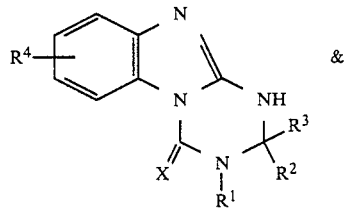

&

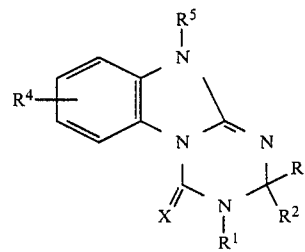

wherein X is oxygen or sulfur;
wherein
R$^1$ is hydrogen, lower alkyl (C$_1$–C$_6$), cycloalkyl (C$_3$–C$_7$) lower alkenyl (C$_2$–C$_6$), lower alkynyl (C$_3$–C$_6$), haloalkyl (C$_1$–C$_6$) and alkoxyalkyl (C$_2$–C$_6$);

R$^2$ and R$^3$ individually are alkyl containing 1–3 carbon atoms and cycloalkyl containing 3–5 carbon atoms, R$^4$ individually can be H, alkyl (C$_1$–C$_6$), a maximum of two halogens selected from the group consisting of Cl, F, and Br, alkoxyl (C$_1$–C$_4$), nitro, alkylthio (C$_1$–C$_4$) and alkylsulfonyl (C$_1$–C$_4$);

R$^5$ may be hydrogen, carbamoyl, N-alkylcarbamoyl (C$_2$–C$_{14}$), N-arylcarbamoyl, N-(substituted aryl)carbamoyl, N-haloalkylcarbamoyl (C$_2$–C$_{12}$), N-carboalkoxyalkylcarbamoyl, N-carboxyalkylcarbamoyl (C$_3$–C$_{14}$), N-alkoxyalkylcarbamoyl (C$_3$–C$_{14}$), N-arylsulfonylcarbamoyl, acyl(C$_1$–C$_{14}$), aroyl, substituted aroyl, alkoxycarbonyl (C$_2$–C$_{14}$), aryloxycarbonyl, hydroxyacyl (C$_2$–C$_8$), alkoxyacyl (C$_3$–C$_9$), alkylthioacyl (C$_3$–C$_9$), alkylsulfonylacyl (C$_3$–C$_7$), N,N-dialkylaminoacyl (C$_4$–C$_{10}$), alkylsulfonyl (C$_1$–C$_{14}$), haloalkylsulfonyl (C$_1$–C$_{14}$), arylsulfonyl, substituted arylsulfonyl, alkyl (C$_1$–C$_{14}$), hydroxyalkyl (C$_1$–C$_8$), alkoxyalkyl (C$_2$–C$_9$), haloalkyl (C$_1$–C$_8$), cycloalkyl (C$_3$–C$_7$), alkenyl (C$_2$–C$_{14}$), cycloalkenyl (C$_5$–C$_7$), alkynyl (C$_2$–C$_{14}$), aryl and substituted aryl.

13. A method according to claim 12 wherein R$^1$ is methyl.

14. A method according to claim 12 wherein R$^4$ is hydrogen.

15. A method for the control of aquatic plant life which comprises applying to the aquatic plant life a composition comprising an inert carrier, and as an essential active ingredient, in a quantity toxic to aquatic plant life 1,2-Dihydro-2,2,3-trimethyl-1,3,5-triazino[1,2-a]benzimidazol-4(3H)-one.

16. A method for the control of aquatic plant life which comprises applying to the aquatic plant life a composition comprising an inert carrier, and as an essential active ingredient, in a quantity toxic to aquatic plant life 1,2-dihydro-2,3-dimethyl-2-ethyl-1,3,5-triazino[1,2-a]benzimidazol-4(3H)-one.

17. A method for the control of aquatic plant life which comprises applying to the aquatic plant life a composition comprising an inert carrier, and as an essential active ingredient, in a quantity toxic to aquatic plant life 4-Oxo-2,3,4,10-tetrahydro-N-2,2,3-tetramethyl-1,3,5-triazino[1,2-a]benzimidazole-10-carboxamide.

18. A method for the control of aquatic plant life which comprises applying to the aquatic plant life a composition comprising an inert carrier, and as an essential active ingredient, in a quantity toxic to aquatic plant life 2-Ethyl-4-oxo-2,3,4,10-tetrahydro-N,2,3-trimethyl-1,3,5-triazino[1,2-a]benzimidazole-10-carboxamide.

19. A method for the control of aquatic plant life which comprises applying to the aquatic plant life a composition comprising an inert carrier, and as an essential active ingredient, in a quantity toxic to aquatic plant life 2,10-Dihydro-10-(methylsulfonyl)-2,2,3-trimethyl-1,3,5-triazino[1,2-a]benzimidazol-4(3H)-one.

20. A method for the control of aquatic plant life which comprises applying to the aquatic plant life a composition comprising an inert carrier, and as an essential active ingredient, in a quantity toxic to aquatic plant life 2,10-Dihydro-10-[(4-tolyl)sulfonyl]-2,2,3-trimethyl-1,3,5-triazino[1,2a]benzimidazol-4(3H)-one.

* * * * *